(12) United States Patent
Kim et al.

(10) Patent No.: US 12,006,308 B2
(45) Date of Patent: Jun. 11, 2024

(54) ADHESIVE COMPOSITION FOR SEMICONDUCTOR CIRCUIT CONNECTION AND ADHESIVE FILM CONTAINING THE SAME

(71) Applicant: LG CHEM, LTD., Seoul (KR)

(72) Inventors: Youngsam Kim, Daejeon (KR); Junghak Kim, Daejeon (KR); Ju Hyeon Kim, Daejeon (KR); Kwang Joo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 881 days.

(21) Appl. No.: 17/047,551

(22) PCT Filed: Oct. 22, 2019

(86) PCT No.: PCT/KR2019/013905
§ 371 (c)(1),
(2) Date: Oct. 14, 2020

(87) PCT Pub. No.: WO2020/085770
PCT Pub. Date: Apr. 30, 2020

(65) Prior Publication Data
US 2021/0115021 A1    Apr. 22, 2021

(30) Foreign Application Priority Data
Oct. 23, 2018 (KR) .................. 10-2018-0126662

(51) Int. Cl.
*C07D 403/12* (2006.01)
*C09J 7/30* (2018.01)
*C09J 11/06* (2006.01)
*C09J 163/00* (2006.01)
*H01L 23/00* (2006.01)

(52) U.S. Cl.
CPC .............. *C07D 403/12* (2013.01); *C09J 7/30* (2018.01); *C09J 11/06* (2013.01); *C09J 163/00* (2013.01); *H01L 24/29* (2013.01)

(58) Field of Classification Search
CPC .... C07D 403/12; C08F 220/34; C08F 220/36; C09D 163/00; C09J 7/00; C09J 7/30; C09J 11/06; C09J 11/08; C09J 163/00; C09J 201/00; C09J 2203/326; H01L 21/67; H01L 24/10; H01L 24/26; H01L 24/29
See application file for complete search history.

(56) References Cited

U.S. PATENT DOCUMENTS

| | | |
|---|---|---|
| 6,822,341 B1 * | 11/2004 | Ahsan .................. C08G 59/686 523/210 |
| 8,536,281 B2 | 9/2013 | Montarnal et al. |
| 2009/0111930 A1 | 4/2009 | Van Gemert et al. |
| 2011/0251364 A1 | 10/2011 | Anthamatten et al. |
| 2015/0125646 A1 | 5/2015 | Tournilhac et al. |
| 2018/0072825 A1 | 3/2018 | Delgado |
| 2019/0043748 A1 | 2/2019 | Kim et al. |

FOREIGN PATENT DOCUMENTS

| | | |
|---|---|---|
| CN | 104231157 A | 12/2014 |
| JP | 2002-194057 A | 7/2002 |
| JP | 2011-522909 A | 8/2011 |
| JP | 2016-540877 A | 12/2016 |
| KR | 10-1234711 B1 | 2/2013 |
| KR | 10-1809935 B1 | 12/2017 |
| TW | 201819578 A | 6/2018 |

OTHER PUBLICATIONS

International Search Report issued for International Application No. PCT/KR2019/013905 dated Feb. 7, 2020, 4 pages.
Heinzmann, C. et al., "Supramolecular polymer adhesives: advanced materials inspired by nature", Chem. Soc. Rev., 2016, vol. 45, pp. 342-358.
Yamauchi, K. et al., "Thermoreversible Poly(alkyl acrylates) Consisting of Self-Complementary Multiple Hydrogen Bonding", Macromolecules, 2003, vol. 36, pp. 1083-1088.
Taiho Park et al., "Formation of a Miscible Supramolecular Polymer Blend through Self-Assembly Mediated by a Quadruply Hydrogen-Bonded Heterocomplex", J. Am. Chem. Soc. 2006, 128, 11582-11590.
Satu Strandman et al., "Self-Healing Supramolecular Hydrogels Based on Reversible Physical Interactions", GELS, 2016, vol. 2, No. 2, pp. 16(1-31).
Michelle H. Wrue, "Synthesis and Phase Behavior of End-Functionalized Associating Polymers", Phd Dissertation, Univ. of Rochester, 2010, 119 pages.
Christian Heinzmann et al., "Supramolecular Polymer Networks Made by Solvent-Free Copolymerization of a Liquid 2-Ureido-4[1H]-pyrimidinone Methacrylamide", Macromolecules 2015, 48, 22, 8128-8136.

\* cited by examiner

*Primary Examiner* — John M Cooney
(74) *Attorney, Agent, or Firm* — ROTHWELL, FIGG, ERNST & MANBECK, P.C.

(57) ABSTRACT

The present disclosure relates to a polymer compound having a specific structure, including an acrylic resin having a functional group capable of mutual hydrogen bonding with an acrylic resin having imidazole, a resin composition for bonding semiconductors including a thermoplastic resin; a thermosetting resin; a curing agent; and the polymer compound having a specific structure, and an adhesive film for semiconductor produced using the same.

9 Claims, No Drawings

ADHESIVE COMPOSITION FOR SEMICONDUCTOR CIRCUIT CONNECTION AND ADHESIVE FILM CONTAINING THE SAME

CROSS-REFERENCE TO RELATED APPLICATION(S)

This application is a 35 U.S.C. 371 National Phase Entry Application from PCT/KR2019/013905 filed on Oct. 22, 2019, designating the United States, which claims priority to or the benefit of Korean Patent Application No. 10-2018-0126662 filed with the Korean Intellectual Property Office on Oct. 23, 2018, the disclosures of which are incorporated herein by reference in their entirety.

TECHNICAL FIELD

The present disclosure relates to an adhesive composition for semiconductor circuit connection and an adhesive film containing the same.

BACKGROUND OF THE INVENTION

Recently, as the tendency toward miniaturization, high functionalization, and large capacity of electronic equipment has been expanding and the need for densification and high integration of a semiconductor package has rapidly increased, the size of semiconductor chips has been becoming larger and larger. In terms of improvement of integration degree, the stack package method for stacking chips in multiple stages has gradually increased.

In addition, recently, a semiconductor using a through silicon via (TSV) has been developed, and signal transmission through bump bonding has been performed. For such bump bonding, thermal compression bonding technology is mainly applied. Herein, the heat curing property of the adhesive in the thermal compression bonding technology affects the package manufacturing processability and package reliability.

A non-conductive paste (NCP) in the form of a paste has been developed as an adhesive for filling between respective TSV layers, but there was a problem that the pitch of the bumps became narrower and the filling became more difficult. In order to overcome these problems, a non-conductive film (NCF) provided in the form of a film has been developed.

During thermal compression bonding for bump bonding, the adhesive must be cured rapidly at high temperatures, curing must be suppressed at room temperature and storage stability should be good. In such adhesives, catalysts play an important role in adjusting the curing degree, and a thermally-latent catalyst for this purpose has been developed.

To this end, the imidazole type, which is a widely used catalyst, has poor compatibility between a solvent and a resin formulation, and thus, there are disadvantages in that the surface condition of the adhesive film is poor, it is difficult to adjust the reactivity by temperature section, and a microreaction occurs at room temperature.

DETAILED DESCRIPTION OF THE INVENTION

The present disclosure provides an adhesive composition for semiconductor circuit connection that enables adjustment of low-temperature and room-temperature stability and high-temperature catalyst activity by using a specific polymer resin as a latent catalyst of a resin composition for bonding semiconductors.

The present disclosure also provides an adhesive film including the aforementioned adhesive composition for semiconductor circuit connection.

One aspect of the present disclosure provides a compound represented by the following Chemical Formula 1:

[Chemical Formula 1]

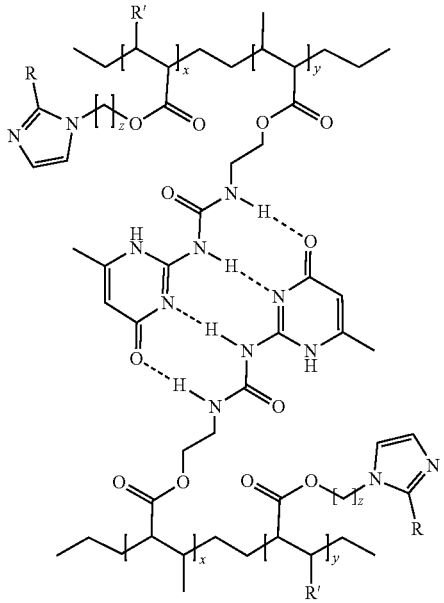

wherein, in Chemical Formula 1,

R and R' are each independently hydrogen, an alkyl group having 1 to 10 carbon atoms, an aryl group having 6 to 20 carbon atoms or a cyclic hydrocarbon having 3 to 8 carbon atoms, wherein in the R and R', the alkyl group, the aryl group or the cyclic hydrocarbon may have each independently a heteroatom, each x is independently 1 to 50, each y is independently 1 to 100 and each z is independently 1 to 4.

More specifically, in Chemical Formula 1, R is hydrogen, x is 1 to 6, y is 8 to 10, and z may be 1 to 4.

Another aspect of the present disclosure provides a method for preparing the compound of Chemical Formula 1, including reacting a compound of the following Chemical Formula 2 with a compound of the following Chemical Formula 3:

[Chemical Formula 2]

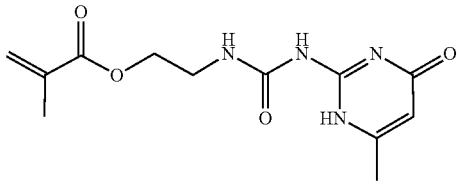

-continued

[Chemical Formula 3]

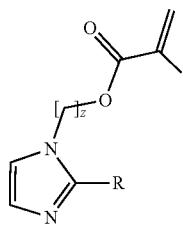

wherein, in Chemical Formula 3,

R and R' are each independently hydrogen, an alkyl group having 1 to 10 carbon atoms, an aryl group having 6 to 20 carbon atoms or a cyclic hydrocarbon having 3 to 8 carbon atoms, wherein in the R and R', the alkyl group, the aryl group or the cyclic hydrocarbon may have each independently a heteroatom, and each z is independently 1 to 4.

In Chemical Formula 3, R is hydrogen, R' is a methyl group, and z may be 1 to 4.

In addition, the method may include reacting 0.1 to 10 equivalent weights of the compound of Chemical Formula 3 with respect to 1 equivalent weight of the compound of Chemical Formula 2.

Another aspect of the present disclosure provides a resin composition for bonding semiconductors including a thermoplastic resin; a thermosetting resin; a curing agent; and the compound of Chemical Formula 1.

The resin composition for bonding semiconductors may include 0.1 to 15 parts by weight of the compound of Chemical Formula 1 relative to 100 parts by weight of the total of the thermoplastic resin; the thermosetting resin; the curing agent; and the compound of Chemical Formula 1.

The thermoplastic resin may include one or more polymer resins selected from the group consisting of polyimide, polyether imide, polyester imide, polyamide, polyether sulfone, polyether ketone, polyolefin, polyvinyl chloride, phenoxy, reactive butadiene-acrylonitrile copolymer rubber and (meth)acrylate-based resin.

The thermosetting resin may include one or more selected from the group consisting of a solid epoxy resin and a liquid epoxy resin.

The curing agent may include a phenol resin having a softening point of 70° C. or higher.

Still another aspect of the present disclosure provides an adhesive film for semiconductor containing the aforementioned resin composition for bonding semiconductors.

Advantageous Effects

According to the present disclosure, an adhesive composition for semiconductor circuit connection and an adhesive film for semiconductor that can induce film curing reaction at various temperatures from low temperature to high temperature by using a polymer compound capable of increasing the compatibility of a latent catalyst, and improving the ability to control the reaction zone for each temperature, can be provided.

DETAILED DESCRIPTION OF THE EMBODIMENTS

Hereinafter, the adhesive composition for semiconductor circuit connection and the adhesive film for semiconductor according to specific embodiments of the present disclosure will be described in more detail. However, these examples are presented for illustrative purposes only, and are not intended to limit the scope of the present disclosure.

According to one embodiment of the present disclosure, there can be provided a compound of the following Chemical Formula 1.

[Chemical Formula 1]

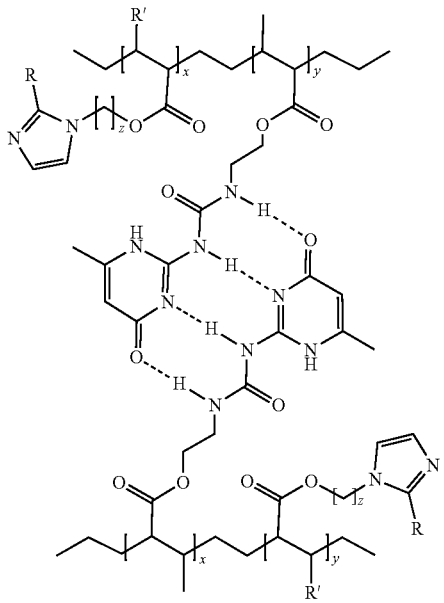

wherein, in Chemical Formula 1,

R and R' are each independently hydrogen, an alkyl group having 1 to 10 carbon atoms, an aryl group having 6 to 20 carbon atoms or a cyclic hydrocarbon having 3 to 8 carbon atoms, wherein in the R and R', the alkyl group, the aryl group or the cyclic hydrocarbon may have each independently a heteroatom, each x is independently 1 to 50, each y is independently 1 to 100 and each z is independently 1 to 4.

The present inventors have conducted research on components that can be used for the bonding or packaging of semiconductor devices, and have found that the compound of Chemical Formula 1 and a composition or adhesive film including the same are applied as materials for semiconductor circuit connection, and thus have excellent storage stability under low temperature and room temperature while being curable at various temperatures.

Specifically, the compound of Chemical Formula 1 may be provided as a latent catalyst by reacting an acryl monomer having an imidazole group with a polymer having a plurality of hydrogen bonds.

Herein, the hetero atom in the present disclosure may include a halogen, O, N, S, P and the like, as is well known.

In addition, in Chemical Formula 1 of the present disclosure, x may represent a ratio of Chemical Formula 2 described later, and y may represent a ratio of Chemical Formula 3 described later.

Preferably, in Chemical Formula 1, R is hydrogen, x is 1 to 6, y is 8 to 10, and z is 1 to 4. As a preferred example, in Chemical Formula 1, R is hydrogen, x is 1, y is 10, and z is 2. As another preferred example, in Chemical Formula 1, R is hydrogen, x is 6, y is 8, and z is 2.

Further, in order to delay/adjust the curing of imidazole, there have been known methods such as encapsulating the imidazole curing agent or storing it in adduct form together with glycidol, but a method of using hydrogen bonding as in the present disclosure has never been studied.

Such a compound of Chemical Formula 1 may limit the role of latent catalysts depending on the conditions and increase thermal stability at low temperatures. Moreover, the compound of Chemical Formula 1 allows the role of the imidazole catalyst to be performed without problems at high temperatures where the reaction needs to proceed, and it can adjust the activity of the catalyst for each temperature range by limiting the number of hydrogen bonds. Therefore, the compound of Chemical Formula 1 of the present disclosure is stable at a low temperature, and may play an excellent role as a latent catalyst capable of adjusting the activity of the catalyst at a high temperature.

That is, when the compound of Chemical Formula 1 of the present disclosure receives heat, the imidazole catalyst structure may be blocked and deactivated from an external material as shown in the following Reaction Schemes 1 and 2, thereby adjusting the role of the latent catalyst.

[Reaction Scheme 1]

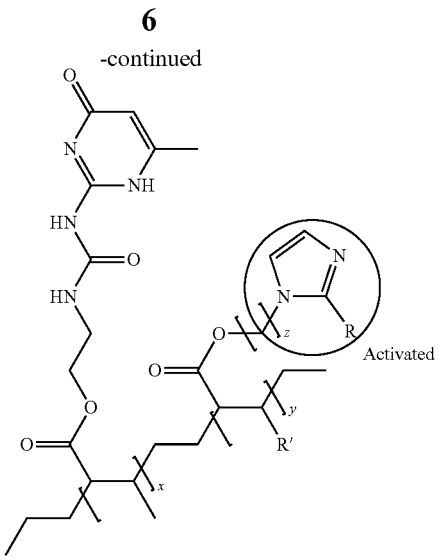

(in Reaction Scheme 1, R, R', x, y and z are the same as defined above).

[Reaction Scheme 2]

In particular, the present invention can combine the catalyst in the form of a branch to two acrylic resin structured oligomers in order to increase the compatibility of the latent catalyst and improve the ability to adjust the reaction zone for each temperature.

Accordingly, the present invention provides an advantage that the film curing reaction can be induced at various temperatures by adjusting the intermolecular forces of the two oligomers including the latent catalyst. Further, the present disclosure can activate the catalyst by utilizing an intermolecular force capable of structurally hydrogen bonding like DNA without using a chemical reaction.

In addition, the compound of Chemical Formula 1 of the present disclosure forms a dimer or trimer-type structure through intermolecular forces such as hydrogen bonds in the resin composition for bonding semiconductors, and thereby allows the catalyst to deactivate at low temperature and room temperature to have the property of delaying the reaction with the epoxy resin.

Moreover, when the compound of Chemical Formula 1 is used as a latent catalyst, the intermolecular force which hinders catalytic activity at high temperature is weakened, and thus can serve as a latent catalyst.

Therefore, the compound of Chemical Formula 1 of the present disclosure can improve the surface state of the adhesive film with excellent compatibility. In particular, it is possible to adjust the reactivity for each temperature section and thus adjust the curing properties according to the temperature conditions of low temperature to high temperature. Further, during thermal compression bonding for bump bonding, the compound of Chemical Formula 1 of the present disclosure can be cured within a short time at high temperature, and curing can be suppressed at low temperature and room temperature to improve storage stability.

Meanwhile, according to another embodiment of the present disclosure, there can be provided a method for preparing the compound of Chemical Formula 1 including reacting a compound of the following Chemical Formula 2 with a compound of the following Chemical Formula 3.

[Chemical Formula 2]

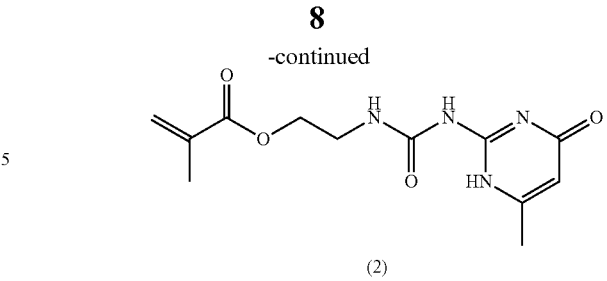

[Chemical Formula 3]

wherein, in Chemical Formula 3,

R and R' are each independently hydrogen, an alkyl group having 1 to 10 carbon atoms, an aryl group having 6 to 20 carbon atoms or a cyclic hydrocarbon having 3 to 8 carbon atoms, wherein in the R and R', the alkyl group, the aryl group or the cyclic hydrocarbon may have each independently a heteroatom, and each x is independently an integer of 1 to 4.

In Chemical Formula 3, R is hydrogen, R' is methyl and z may be 1 to 4. Most preferably, in Chemical Formula 3, R is hydrogen, R' is methyl, and z may be 2.

[Reaction Scheme 3]

[Reaction Scheme 4]

(in Reaction Scheme 4, R, R' and z are the same as defined above, and X is a halogen atom)

Such a method of the present disclosure may include reacting 0.1 to 10 equivalent weights of the compound of Chemical Formula 3 with respect to 1 equivalent weight of the compound of Chemical Formula 2. Herein, if the content of the compound of Chemical Formula 3 is less than 0.1 equivalent weight, there is a problem that it is necessary to include an excess catalyst in the composition in order to serve as a catalyst. If the content is more than 10 equivalent weights, the hydrogen bond may be weakened due to the reduction of the hetero elements in Chemical Formula 2, which may cause a problem when serving as a latent catalyst.

That is, in Chemical Formula 1, x may represent a ratio of Chemical Formula 3, and y may represent a ratio of Chemical Formula 2, and therefore, by adjusting the content of the compound of Chemical Formula 3, the compound of Chemical Formula 1 of interest may be provided.

Meanwhile, according to another aspect of the present disclosure, there can be provided a resin composition for bonding semiconductors including a thermoplastic resin; a thermosetting resin; a curing agent; and the compound of Chemical Formula 1.

The resin composition for bonding semiconductors may include 0.1 to 15 parts by weight, or 0.5 to 10 parts by weight, of the compound of Chemical Formula 1 relative to 100 parts by weight of the total of the thermoplastic resin; the thermosetting resin; the curing agent; and the compound of Chemical Formula 1.

When the weight of the compound of Chemical Formula 1 relative to 100 parts by weight of the total of the thermoplastic resin; the thermosetting resin; the curing agent; and the compound of Chemical Formula 1 is too low, it is difficult for the curing reaction to proceed and so the curing is not ensured, or the reaction temperature interval widely appears, and the rapid curing characteristics that are rapidly cured at a specific temperature may be lost.

When the weight of the compound of Chemical Formula 1 relative to 100 parts by weight of the total of the thermoplastic resin; the thermosetting resin; the curing agent; and the compound of Chemical Formula 1 is too high, some catalysts are activated even at room temperature and the reaction may proceed, so the storage stability of the film may not be secured.

Meanwhile, according to the embodiment of the present disclosure, the adhesive composition for semiconductor circuit connection may, in addition to the compound of Chemical Formula 1, further include a thermoplastic resin, a thermosetting resin and an inorganic filler.

Further, the adhesive composition for semiconductor circuit connection may, in addition to the compound of Chemical Formula 1, further include a thermosetting resin, a thermoplastic resin, a curing agent, and an inorganic filler.

As the thermoplastic resin, the thermosetting resin and the inorganic filler contained in the adhesive composition for bonding semiconductors of the embodiment, components commonly known in the field of adhesive compositions for semiconductor circuit connection can be applied.

Examples of the thermosetting resin are not particularly limited, and for example, an epoxy resin can be preferably applied as the thermosetting resin.

Specifically, the epoxy resin may be one or more selected from the group consisting of bisphenol-based epoxy resin, biphenyl-based epoxy resin, naphthalene-based epoxy resin, florene-based epoxy resin, phenol novolac-based epoxy resin, cresol novolac-based epoxy resin, trishydroxyphenyl-methane-based epoxy resin, tetraphenylmethane-based epoxy resin, dicyclopentadiene type epoxy resin, and dicyclopentadiene-modified phenol type epoxy resin Here, the bisphenol-based epoxy resin may include bisphenol A type epoxy resin, bisphenol F type epoxy resin, bisphenol S type epoxy resin, hydrogenated bisphenol A type epoxy resin, bisphenol AF type epoxy resin, and the like.

As a non-limiting example, when two types of epoxy resins are applied as the thermosetting resin, an epoxy resin that is a liquid at 10 to 35° C. and an epoxy resin that is a solid at 10 to 35° C. may be used by mixing at a weight ratio of 1:0.1 to 1:5.

Herein, if the content of the solid epoxy resin is less than 0.1 weight ratio with respect to the liquid epoxy resin, the resin may excessively flow out in die attach processes which may cause contamination, and the stickiness of the adhesive layer is strong which may remarkably reduce the pickup property. On the other hand, when the content of the solid epoxy resin exceeds 5.0 weight ratio with respect to the liquid epoxy resin, it may be disadvantageous in terms of compatibility and reactivity with the thermoplastic resin.

And, the epoxy resin may further include one or more epoxy resins selected from the group consisting of a cresol novolac type epoxy resin having a softening point of 50° C. to 100° C. and a bisphenol A epoxy resin having a softening point of 50° C. to 100° C. together with a biphenyl-based epoxy resin having a softening point of 50° C. to 100° C.

Herein, the epoxy resin may include one or more epoxy resins selected from the group consisting of the cresol novolac type epoxy resin having a softening point of 50° C. to 100° C. and the bisphenol A epoxy resin having a softening point of 50° C. to 100° C. in a weight ratio of 0.25 to 1.25, or 0.3 to 1.1 relative to the biphenyl-based epoxy resin having a softening point of 50° C. to 100° C.

The epoxy resin may have an average epoxy equivalent weight of 100 to 1,000. The average epoxy equivalent weight may be determined based on the weight ratio and epoxy equivalent weight of each epoxy resin contained in the epoxy resin.

The type of the thermoplastic resin is also not particularly limited, and for example, it may include one or more polymer resins selected from the group consisting of polyimide, polyether imide, polyester imide, polyamide, polyether sulfone, polyether ketone, polyolefin, polyvinyl chloride, phenoxy, reactive butadiene-acrylonitrile copolymer rubber and (meth)acrylate resin.

Preferably, as the thermoplastic resin, a (meth)acrylate-based resin having a glass transition temperature of −10 to 30° C. and a weight average molecular weight of 200,000 to 1,000,000 g/mol can be applied.

The acrylic-based resin is an epoxy group-containing acrylic copolymer, and may contain 1 to 25% by weight, or 2 to 20% by weight, or 2.5 to 15% by weight of glycidyl acrylate or glycidyl methacrylate in the total weight.

Here, when the content of the epoxy group in the (meth) acrylate-based resin is less than 1% by weight, compatibility and adhesive force with the epoxy resin are not sufficient. When the content exceeds 25% by weight, the viscosity rise rate due to curing may be too high, so that solder bumps may not be sufficiently bonded and embedded in the thermal compression bonding process of the semiconductor device.

The thermoplastic resin may be included in an amount of 10 to 1,500 parts by weight based on 100 parts by weight of the thermosetting resin in consideration of flow control and the like of the composition during manufacture of the adhesive film.

As the curing agent, compounds known to be able to function as a curing agent of the thermosetting resin can be used. More specifically, the curing agent may include one or more compounds selected from the group consisting of an amine-based curing agent, and an acid anhydride-based curing agent.

As the curing agent, a novolac-based phenol resin may be preferably applied.

The novolac-based phenol resin has a chemical structure in which a ring is located between the reactive functional groups. Due to these structural characteristics, the novolac-based phenol resin can further reduce the hygroscopicity of the adhesive composition, and can further improve the stability in the high temperature IR reflow process. Thus, it can play a role of preventing peeling phenomenon, reflow cracking, etc. of the adhesive film.

Specific examples of the novolac-based phenol resin may include one or more selected from the group consisting of novolac phenolic resin, Xylok novolac phenolic resin, cresol novolac phenolic resin, biphenyl novolac phenolic resin, bisphenol A novolac phenolic resin, and bisphenol F novolac phenolic resin.

As the novolac-based phenol resin, those having a softening point of 60° C. or higher, or 60° C. to 150° C., or 105° C. to 150° C., or 70° C. to 120° C. can be preferably applied. The novolac-based phenol resin having a softening point of 60° C. or higher is designed to have sufficient heat resistance, strength and adhesiveness after curing of the adhesive composition. However, if the softening point of the novolac-based phenol resin is too high, the fluidity of the adhesive composition is reduced, and voids are generated inside the adhesive in the actual semiconductor manufacturing process, which may greatly reduce the reliability or quality of a final product.

The novolac-based phenol resin preferably has a hydroxyl equivalent weight of 80 g/eq to 300 g/eq and a softening point of 60° C. to 150° C.

The content of the curing agent may be appropriately selected in consideration of the physical properties of a finally produced adhesive film. For example, the curing agent may be used in an amount of 10 to 700 parts by weight or 30 to 300 parts by weight based on 100 parts by weight of the thermosetting resin.

The composition for bonding semiconductors may further include a curing catalyst.

The curing catalyst plays serves to promote the action of the curing agent or curing of the resin composition for bonding semiconductors, and curing catalysts known to be used in the production of semiconductor adhesive films and the like can be used without particular limitation.

For example, as the curing catalyst, one or more selected from the group consisting of phosphorus-based compounds, boron-based compounds, phosphorus-boron based compounds, and imidazole-based compounds can be used. The amount of the curing agent used may be appropriately selected in consideration of the physical properties of a finally produced adhesive film.

Meanwhile, the resin composition for bonding semiconductors of the embodiment may further include an inorganic filler.

As the inorganic filler, one or more inorganic particles selected from the group consisting of alumina, silica, barium sulfate, magnesium hydroxide, magnesium carbonate, magnesium silicate, magnesium oxide, calcium silicate, calcium carbonate, calcium oxide, aluminum hydroxide, aluminum nitride, and aluminum borate can be applied.

An ion adsorbent that can adsorb ionic impurities to improve reliability can also be used as the inorganic filler. As the ion adsorbent, one or more inorganic particles selected from the group consisting of magnesium types such as magnesium hydroxide, magnesium carbonate, magnesium silicate or magnesium oxide, calcium silicate, calcium carbonate, calcium oxide, alumina, aluminum hydroxide, aluminum nitride, aluminum borate whisker, zirconium-based inorganic material, and antimony bismuth-based inorganic material can be applied.

As the inorganic filler, those having an average particle size (based on the longest outer diameter) of 0.01 to 10 μm, 0.02 to 5.0 μm, or 0.03 to 2.0 μm can be preferably applied. If the particle size of the inorganic filler is too small, it can be easily aggregated in the adhesive composition. On the other hand, if the particle size of the inorganic filler is too large, damage to the semiconductor circuit and deterioration in adhesion of the adhesive film may be caused by the inorganic filler.

The inorganic filler may be used in an amount of 10 to 300 parts by weight or 15 to 250 parts by weight based on 100 parts by weight of the total of the thermosetting resin and the thermoplastic resin.

Further, the adhesive composition for semiconductor circuit connection may include 10 to 90 parts by weight of an organic solvent based on 100 parts by weight of the total of the thermosetting resin, the thermoplastic resin, and the inorganic filler. The content of the organic solvent may be determined in consideration of the physical properties or the production process of the adhesive composition and the finally produced adhesive film.

The organic solvent may be one or more compounds selected from the group consisting of esters, ethers, ketones, aromatic hydrocarbons, and sulfoxides.

The ester solvent may be ethyl acetate, acetic acid-n-butyl, isobutyl acetate, amyl formate, isoamyl acetate, isobutyl acetate, butyl propionate, isopropyl butyrate, ethyl butyrate, butyl butyrate, methyl lactate, ethyl lactate, gamma-butyrolactone, epsilon-caprolactone, delta-valerolactone, alkyl oxyacetate (e.g. methyl oxyacetate, ethyl oxyacetate, butyl oxyacetate (e.g., methyl methoxyacetate, ethyl methoxyacetate, butyl methoxyacetate, methyl ethoxyacetate, ethyl ethoxyacetate, etc.)), 3-oxypropionic acid alkyl ester (e.g., methyl 3-oxypropionate, ethyl 3-oxypropionate, etc. (e.g., methyl 3-methoxypropionate, ethyl 3-methoxypropionate, methyl 3-ethoxypropionate, ethyl 3-ethoxypropionate, etc.)), 2-oxypropionic acid alkyl ester (e.g. methyl 2-oxypropionate, ethyl 2-oxypropionate, propyl 2-oxypropionate and the like (e.g., methyl 2-methoxypropionate, ethyl 2-methoxypropionate, propyl 2-methoxypropionate, methyl 2-ethoxypropionate, ethyl 2-ethoxypropionate)), methyl 2-oxy-2-methylpropionate and ethyl 2-oxy-2-methylpropionate (e.g., methyl 2-methoxy-2-methylpropionate, ethyl 2-ethoxy-2-methylpropionate, etc.), methyl pyruvate, ethyl pyruvate, propyl pyruvate, methyl acetoacetate, ethyl acetoacetate, methyl 2-oxobutyrate, ethyl 2-oxobutyrate, or the like.

The ether solvent may be diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, or the like.

The ketone solvent may be methyl ethyl ketone, cyclohexanone, cyclopentanone, 2-heptanone, 3-heptanone, N-methyl-2-pyrrolidone, or the like.

The aromatic hydrocarbon solvent may be toluene, xylene, anisole, limonene, or the like.

The sulfoxide solvent may be dimethyl sulfoxide or the like.

In addition, the adhesive composition for semiconductor circuit connection may include a coupling agent. The type of the coupling agent is not particularly limited, but preferably, 2-(3,4-epoxycyclohexyl)ethyltrimethoxysilane, 3-glycidoxypropyltrimethoxysilane, 3-glycidoxypropylmethyl-diethoxysilane, 3-glycidoxypropyltriethoxysilane, N-(2-aminoethyl)-3-aminopropylmethyldimethoxysilane, N-(2-aminoethyl)-3-aminopropyltrimethoxysilane, N-(2-aminoethyl)-3-aminopropyltriethoxysilane, 3-aminopropyltrimethoxysilane, 3-aminopropyltriethoxysilane, 3-triethoxyl-N-(1,3-dimethylbutylidene)propylamine, N-phenyl-3-aminopropyltrimethoxysilane, mercapto-containing 3-mercaptopropylmethyldimethoxysilane, 3-mercaptopropyltrimethoxysilane, or the like can be applied.

According to another embodiment of the present disclosure, there is provided an adhesive film for semiconductor circuit connection including the aforementioned adhesive composition.

As the adhesive film for semiconductor circuit connection includes the adhesive composition for semiconductor circuit connection of the above-described embodiment, it can exhibit excellent curing properties while exhibiting excellent storage stability under low temperature and room temperature.

As a substrate for supporting the aforementioned film, a resin film having excellent heat resistance and chemical resistance; a crosslinked film obtained by crosslinking a resin constituting the resin film; or a film that has been subjected to a release treatment by applying a silicone resin or the like onto the surface of the said resin film, or the like can be used.

As the resin constituting the resin film, polyolefins such as polyester, polyethylene, polypropylene, polybutene, or polybutadiene, vinyl chloride, ethylene-methacrylic acid copolymer, ethylene vinyl acetate copolymer, polyester, polyimide, polyethylene terephthalate, polyamide, polyurethane, or the like can be applied.

The thickness of the supporting substrate is not particularly limited, but may be 3 to 400 µm, or 5 to 200 µm, or 10 to 150 µm.

The adhesive layer consists of the aforementioned adhesive composition. The details regarding the adhesive composition are the same as described above.

Moreover, an adhesive layer may be interposed between the supporting substrate and the adhesive layer as needed. As the adhesive layer, those known in the art may be applied without particular limitation.

The type of the protective film is not particularly limited, and a plastic film known in the art may be applied. For example, the protective film may be a plastic film containing a resin such as low-density polyethylene, linear polyethylene, medium-density polyethylene, high-density polyethylene, ultra-low density polyethylene, polypropylene random copolymer, polypropylene block copolymer, homopolypropylene, polymethylpentene, ethylene-vinyl acetate copolymer, ethylene-methacrylic acid copolymer, ethylene-methylmethacrylate copolymer, ethylene-ionomer copolymer, ethylene-vinyl alcohol copolymer, polybutene, styrene copolymer, or the like.

The adhesive film for semiconductor circuit connection may be prepared by a method including mixing the components of the adhesive composition, coating the mixture on a supporting substrate to a predetermined thickness to form an adhesive layer, and drying the adhesive layer.

Further, the adhesive film may be prepared by a method including forming an adhesive layer on the supporting substrate and then laminating a protective film on the adhesive layer.

Moreover, the adhesive film may be prepared by a method including forming an adhesive layer on the supporting substrate, and then sequentially laminating an adhesive layer and a protective film on the adhesive layer.

As the method for forming an adhesive layer on a supporting substrate, a method of coating the adhesive composition as it is, or diluting it in an appropriate organic solvent and coating it on the supporting substrate or the release film by a known means such as a comma coater, a gravure coater, a die coater, a reverse coater, and the like, and then drying the result at a temperature of 60° C. to 200° C. for 10 seconds to 30 minutes may be used.

If necessary, an aging process may be further performed for progressing a sufficient crosslinking reaction of the adhesive layer.

The thickness of the adhesive layer may be appropriately adjusted in the range of 1 to 500 µm, or 5 to 100 µm, or 5 to 50 µm.

Specific embodiments of the present disclosure are described in more detail by way of examples. However, these examples are merely to illustrate specific embodiments of the present disclosure, and are not intended to limit the scope of the present disclosure.

Preparation Example 1 (Preparation Method of Chemical Formula 1)

The compound of Chemical Formula 1-1 was prepared by the method of the following Reaction Scheme.

(1) Preparation of Chemical Formula 2

2-Amino-4-hydroxy-6-methylpyrimidine and 2-isocyanatoethyl methacrylate were purchased from Sigma Aldrich.

4.0 g of 2-amino-4-hydroxy-6-methylpyrimidine was dissolved in DMSO solution, and then reacted with 5.5 g of 2-isocyanoethyl methacrylate at a temperature of 170° C., and the reaction was immediately terminated using a water bath to produce a compound of Chemical Formula 2.

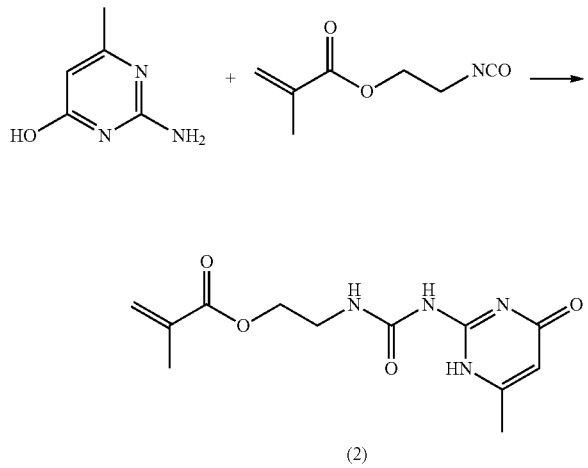

(2) Preparation of Chemical Formula 3

1-(2-Hydroxyethyl)imidazole and methacryloyl chloride were purchased from Sigma Aldrich.

The above two materials were reacted under triethylamine and chloroform solvent at room temperature to produce a compound of Chemical Formula 3.

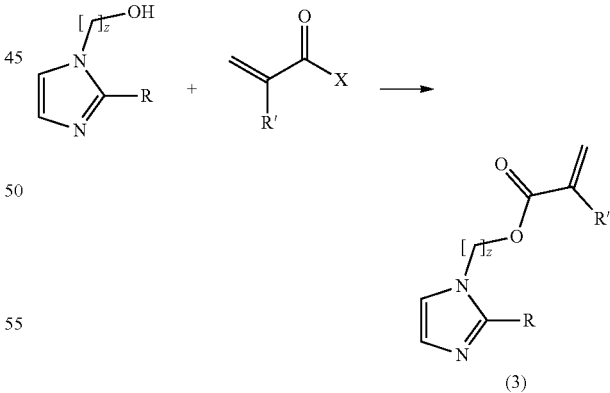

(in Reaction Scheme 4-1, X is Cl, R is H, R' is methyl and z is 2).

(3) Preparation of Chemical Formula 1-1

Compound 2 was reacted with 10 mol % of Compound 2 by free radical copolymerization under the conditions of 0.5 mol % of AIBN and DMSO solvent to produce a compound of Chemical Formula 1-1.

[Chemical Formula 1-1]

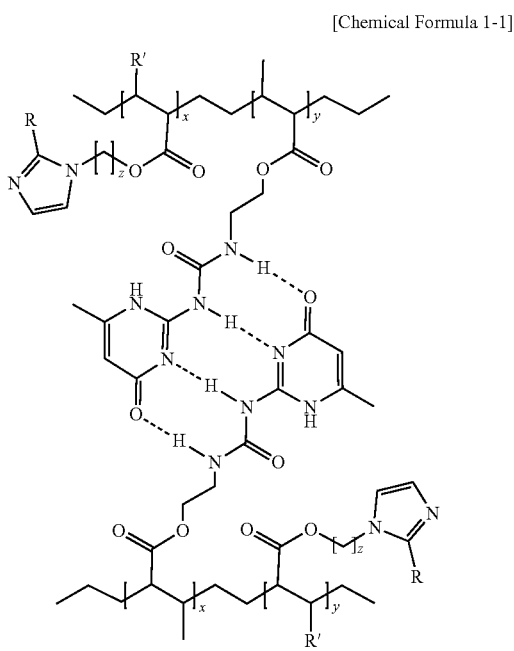

wherein, in Chemical Formula 1,
R is each H, R' is methyl,
each x is independently 1,
each y is independently 10, and
each Z is independently 2.

Example 1: Preparation of Resin Composition for Bonding Semiconductors and Adhesive Film (1) Preparation of Adhesive Composition for Semiconductor Circuit Connection 47 g of phenol resin KH-6021 (produced by DIC Corp., bisphenol A novolac resin, hydroxyl equivalent weight: 121 g/eq, softening point: 133° C.), which is a curing agent for epoxy resin; 40 g of high viscosity liquid epoxy resin RE-310S (produced by Nippon Kayaku Co., Ltd., bisphenol A epoxy resin, epoxy equivalent weight: 180 g/eq); 40 g of thermoplastic acrylate resin KG-3015 (Mw: 900,000, glass transition temperature: 10° C.); 6.0 g of a compound of Chemical Formula 1-1; and 80 g of an inorganic filler SC-2050 (Admatec, spherical silica, average particle size of about 400 nm) were mixed in a methyl ethyl ketone to obtain an adhesive composition for semiconductor circuit connection (solid content: 40 wt % concentration).

(2) Preparation of Adhesive Film

The above-prepared adhesive composition was coated on a release-treated polyethylene terephthalate film (thickness 38 μm), and then dried at 110° C. for 3 minutes to obtain an adhesive film formed from an adhesive layer with a thickness of about 20 μm.

(3) Manufacture of Semiconductor Device

A wafer containing bump chips (4.5 mm×4.5 mm), which is a semiconductor device in which lead-free solder was formed at a height of 3 μm on a copper filler having a height of 15 μm and a pitch of 50 μm, was prepared.

The adhesive layer of the adhesive film was set to be located on the bump surface of the wafer, and vacuum lamination was performed at 50° C., and then singulated into chips.

The singulated bump chip were bonded by thermal compression onto a 6 mm×8 mm substrate chip having a connection pad (pitch 50 μm) using a thermal compression bonder. In this case, the conditions were as follows: temporally bonded under 100N for 2 seconds at a head temperature of 100° C. and allowed to stand at 100° C. for 10 minutes, and then the head temperature was instantaneously increased to 260° C., and thermal compression bonding was performed under 100 N for 4 seconds.

Examples 2 to 3 and Comparative Examples 1 to 4

The adhesive composition for semiconductor circuit connection and the adhesive film using the same were prepared in the same manner as in Example 1, except that the components and contents shown in Tables 1 and 2 were applied. Subsequently, a semiconductor device was manufactured using the same.

TABLE 1

| weight (g) | | Example 1 | Example 2 | Example 3 |
|---|---|---|---|---|
| Phenol resin | KH-6021 | 40 | 40 | 40 |
| Epoxy resin | RE-310S | 40 | 40 | 40 |
| Acrylic resin | KG-3015 | 40 | 40 | 40 |
| Formula 1-1 | | 3 | 6 | 9 |
| Coupling agent | KBM-403 | 1 | 1 | 1 |
| Filler | SC-2050 | 80 | 80 | 80 |

TABLE 2

| weight (g) | | Comparative Example 1 | Comparative Example 2 | Comparative Example 3 | Comparative Example 4 |
|---|---|---|---|---|---|
| Phenol resin | KH-6021 | 40 | 40 | 40 | 40 |
| Epoxy resin | RE-310S | 40 | 40 | 40 | 40 |
| Acrylic resin | KG-3015 | 40 | 40 | 40 | 40 |
| Catalyst | 2MZ-H | — | 1.5 | — | — |
| | 2PZ | — | — | 1.5 | — |
| | 2-(2-Methylphenyl)-1H-imidazole | 1.5 | — | — | — |
| | 3-(1H-Imidazol-2-yl)benzoic acid | — | — | — | 1.5 |
| Coupling agent | KBM-403 | 1 | 1 | 1 | 1 |
| Filler | SC-2050 | 80 | 80 | 80 | 80 |

* KH-6021: phenol resin (DIC, hydroxyl equivalent weight: 121 g/eq, softening point: 133° C.)
* RE-310S: epoxy resin (Nippon Kayaku, epoxy equivalent weight: 180 g/eq)
* KG-3015: acrylate-based resin (including 3% by weight of glycidyl methacrylate repeating unit, glass transition temperature: 10° C., weight average molecular weight: 900,000)
* 2MZ-H: imidazole curing accelerator (Curezol 2MZ-H, SHIKOKU)
* 2PZ: imidazole curing accelerator (Curezol 2PZ, SHIKOKU)
* 2-(2-Methylphenyl)-1H-imidazole: imidazole curing accelerator (Aldrich)
* 3-(1H-Imidazol-2-yl)benzoic acid: imidazole cure accelerator (Formula 1-1 and isomer, Aldrich)
* KBM-403: coupling agent (Epoxy-based, 3-glycidoxypropyl trimethoxysilane, Shin-Etsu Chemical Co., Ltd.)
* SC-2050: filler (Admatec, spherical silica, average particle size: about 400 nm)

Experimental Example: Physical Property Evaluation

Test Example (1) Measurement of Melt Viscosity

The adhesive layers respectively obtained in Examples and Comparative Examples was overlapped and laminated until the thickness became 320 μm, and then laminated using a roll laminator at 60° C. Then, each specimen was molded into a circular shape having a diameter of 8 mm, and then applied to a temperature rise rate of 10° C./min at a shear rate of 5 rad/s using TA Instruments ARES (advanced rheometric expansion system), and the viscosity value of the lowest measured value was judged as melt viscosity.

(2) Evaluation of Voids

The semiconductor devices respectively obtained in Examples and Comparative Examples were observed using a Scanning Acoustic Tomography (SAT), and was evaluated as either "acceptable" (○) if the area of voids between the bump chip and the substrate chip was no greater than 1%, or "unacceptable" (X) if it was greater than 1%.

(3) Electrical Evaluation

The semiconductor devices respectively obtained in Examples and Comparative Examples were evaluated as either "acceptable" (○) if daisy chain connection could be confirmed, or "unacceptable" (X) if daisy chain connection could not be confirmed.

(4) Evaluation of Connection Condition

The connecting part in the semiconductor devices respectively obtained in Examples and Comparative Examples was exposed by cross-sectional polishing, and observed using an optical microscope. An evaluation of "acceptable" (○) was assigned if no trapping was seen in the connecting part and the solder had sufficiently wetted the wiring, while otherwise an evaluation of "unacceptable" (X) was assigned.

(5) Evaluation of Room-Temperature Stability with Time

The adhesive films respectively obtained in Examples and Comparative Examples were allowed to stand at 25° C., and then the variation of ΔH peak was calculated using a differential thermal analyzer (DTA) on a daily basis, and the variation in the minimum melt viscosity was calculated by the above method for measuring the minimum melt viscosity.

When the change rate in the case of the ΔH peak was changed by more than 20% or when the change rate in the case of the minimum melt viscosity was changed by 50% or more, it was judged that there was a change with time. It was evaluated as either "acceptable" (○) if there was a change over 4 weeks, or "unacceptable" (X) if there was a change within 4 weeks.

(6) Evaluation of Stage Stability

When the adhesive films respectively obtained in Examples and Comparative Examples were subjected to isothermal experiments at 80° C. by a differential thermal analysis (DTA) for 8 hours and 24 hours, respectively, the results shown in Tables 3 and 4 below were obtained. The variation of ΔH peak was calculated from the above results. An evaluation of "acceptable" (○) was assigned if the change rate from the existing ΔH peak was 2% or less and 10% or less at the same time, while otherwise an evaluation of "unacceptable" (X) was assigned.

(7) Evaluation of Catalytic Reaction Delay

When the Onset Temperature obtained by the differential thermal analyzer (DTA) was measured for the adhesive films respectively obtained in Examples and Comparative Examples, the results shown in Tables 3 and 4 below were obtained. In the above results, it was evaluated as either "acceptable" (○) if the temperature was 160° C. or more, or "unacceptable" (X) if the temperature was less than that.

TABLE 3

Stage Stability

| Product name | Example 1 | Example 2 | Example 3 |
|---|---|---|---|
| Curing equipment | DTA Cure | DTA Cure | DTA Cure |
| delta H (J/g) | 97 | 106 | 104 |
| Onset T (° C.) | 167 | 168 | 163 |
| ΔH after 8 h @80° C. | 95 | 104 | 102 |
| ΔH after 32 h @80° C. | 88 | 98 | 93 |
| Degree of Cure 8 h @80° C. | 2% | 2% | 2% |
| Degree of Cure 32 h @80° C. | 9% | 8% | 11% |

TABLE 4

Stage Stability

| Product name | Comparative Example 1 | Comparative Example 2 | Comparative Example 3 | Comparative Example 4 |
|---|---|---|---|---|
| Curing equipment | DTA Cure | DTA Cure | DTA Cure | DTA Cure |
| delta H (J/g) | 104 | 106 | 97 | 77 |
| Onset T (° C.) | 158 | 166 | 150 | 154 |
| ΔH after 8 h @80° C. | 96 | 105 | 94 | 71 |
| ΔH after 24 h @80° C. | 88 | 92 | 85 | 66 |
| Degree of Cure 8 h @80° C. | 8% | 1% | 3% | 7% |
| Degree of Cure 24 h @80° C. | 15% | 13% | 12% | 14% |

TABLE 5

| | Example 1 | Example 2 | Example 3 |
|---|---|---|---|
| Melt viscosity (Pa · s) | 11860 | 12240 | 12520 |
| Voids | ○ | ○ | ○ |
| Electrical | ○ | ○ | ○ |
| Connection Condition | ○ | ○ | ○ |
| Room-temperature stability with time | ○ | ○ | ○ |
| Stage stability | ○ | ○ | X |
| Catalytic reaction delay | ○ | ○ | ○ |

TABLE 6

| | Comparative Example 1 | Comparative Example 2 | Comparative Example 3 | Comparative Example 4 |
|---|---|---|---|---|
| Melt viscosity (Pa · s) | 11200 | 9200 | 9000 | 6200 |
| Voids | ○ | ○ | ○ | ○ |
| Electrical | ○ | ○ | ○ | ○ |
| Connection condition | ○ | ○ | ○ | ○ |
| Room-temperature stability with time | X | ○ | ○ | X |
| Stage stability | X | X | X | X |
| catalytic reaction delay | X | ○ | X | X |

As a result of the experiment, it was confirmed that in the case of Comparative Examples 1 to 4, the catalyst reaction delay and the stage stability were insufficient, compared to the case of using the compound of Chemical Formula 1 of Examples 1 to 3 of the present disclosure as a latent catalyst.

The invention claimed is:

1. A compound represented by Chemical Formula 1:

[Chemical Formula 1]

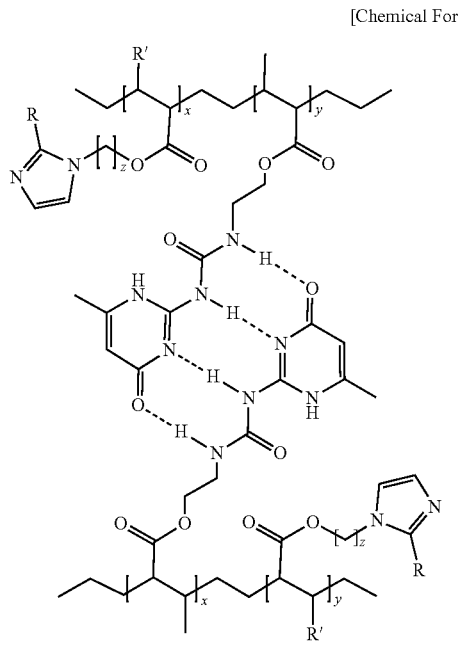

wherein, in the Chemical Formula 1,

R and R' are each independently hydrogen, an alkyl group having 1 to 10 carbon atoms, an aryl group having 6 to 20 carbon atoms or a cyclic hydrocarbon having 3 to 8 carbon atoms, wherein the alkyl group, the aryl group or the cyclic hydrocarbon optionally contains a heteroatom, each x is independently 1 to 50,
each y is independently 1 to 100 and
each z is independently 1 to 4.

2. The compound of claim 1, wherein R is hydrogen, x is 1 to 6, y is 8 to 10, and z is 1 to 4.

3. The compound of claim 1, wherein R is hydrogen, x is 1, y is 10, and z is 2.

4. The compound of claim 1, wherein R is hydrogen, x is 6, y is 8, and z is 2.

5. A method for preparing the compound of Chemical Formula 1 of claim 1, comprising reacting a compound of Chemical Formula 2 with a compound of Chemical Formula 3:

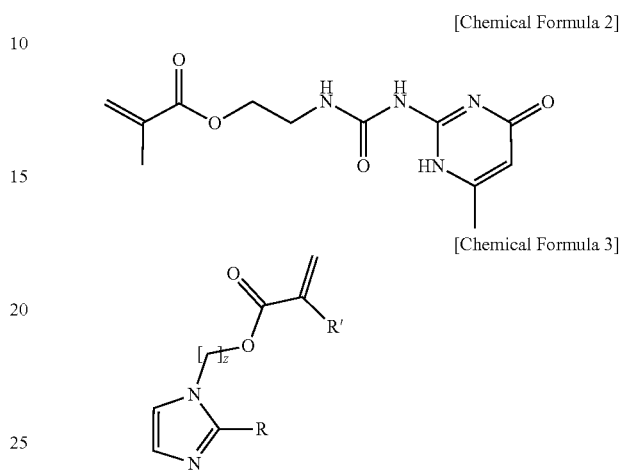

wherein, in the Chemical Formula 3,

R and R' are each independently hydrogen, an alkyl group having 1 to 10 carbon atoms, an aryl group having 6 to 20 carbon atoms or a cyclic hydrocarbon having 3 to 8 carbon atoms, wherein the alkyl group, the aryl group or the cyclic hydrocarbon optionally contains a heteroatom, and each z is independently 1 to 4.

6. The method of claim 5, wherein in the Chemical Formula 3, R is hydrogen, R' is a methyl group, and z is 1 to 4.

7. The method of claim 5, comprising reacting 0.1 to 10 equivalent weights of the compound of Chemical Formula 3 with respect to 1 equivalent weight of the compound of Chemical Formula 2.

8. The compound of claim 1, wherein the heteroatom is a halogen, O, N, S or P.

9. The method of claim 5, wherein the heteroatom is a halogen, O, N, S or P.

* * * * *